United States Patent
Choudhury et al.

(10) Patent No.: US 12,082,861 B2
(45) Date of Patent: Sep. 10, 2024

(54) CABLE PASSER DEVICE

(71) Applicants: Sambhu N. Choudhury, Cincinnati, OH (US); Arturo David Sanchez, Lebanon, OH (US)

(72) Inventors: Sambhu N. Choudhury, Cincinnati, OH (US); Arturo David Sanchez, Lebanon, OH (US)

( * ) Notice: Subject to any disclaimer, the term of this patent is extended or adjusted under 35 U.S.C. 154(b) by 374 days.

(21) Appl. No.: 17/316,888

(22) Filed: May 11, 2021

(65) Prior Publication Data
US 2021/0346073 A1 Nov. 11, 2021

Related U.S. Application Data

(60) Provisional application No. 63/022,768, filed on May 11, 2020.

(51) Int. Cl.
*A61B 17/88* (2006.01)
*A61B 17/82* (2006.01)

(52) U.S. Cl.
CPC .......... *A61B 17/8861* (2013.01); *A61B 17/82* (2013.01)

(58) Field of Classification Search
CPC ............................ A61B 17/82; A61B 17/8861
See application file for complete search history.

(56) References Cited

U.S. PATENT DOCUMENTS

| | | | | | |
|---|---|---|---|---|---|
| 2,897,820 | A | * | 8/1959 | Tauber | A61B 17/0482 606/224 |
| 4,312,337 | A | * | 1/1982 | Donohue | A61B 17/1796 606/103 |
| 4,606,335 | A | * | 8/1986 | Wedeen | A61B 17/04 606/103 |
| 5,544,664 | A | * | 8/1996 | Benderev | A61B 17/42 128/898 |
| 5,851,209 | A | * | 12/1998 | Kummer | A61B 17/149 606/103 |
| 8,282,643 | B2 | * | 10/2012 | Dross | A61B 17/1684 606/86 R |
| 2001/0002436 | A1 | * | 5/2001 | Bowman | A61B 17/0469 606/232 |

(Continued)

FOREIGN PATENT DOCUMENTS

| | | | | | |
|---|---|---|---|---|---|
| EP | 792621 | A1 | * | 9/1997 | ......... A61B 17/0469 |
| GB | 2214814 | A | * | 9/1989 | ......... A61B 17/0482 |
| GB | 2576187 | A | * | 2/2020 | ......... A61B 17/0482 |

*Primary Examiner* — David W Bates
(74) *Attorney, Agent, or Firm* — Jenei LLC

(57) ABSTRACT

The present invention discloses a cable passer device and method for placement of a cerclage cable for internal fixation of bone. The device comprises a cannulated body including a proximal end, a straight portion, an arcuate portion, and a distal end. The straight portion extends from the proximal end, and the arcuate portion extends from the straight portion and ends at the distal end of the cannulated body. A continuous groove extends from the proximal end to the distal end through the straight portion and the arcuate portion of the cannulated body. The groove extends radially along an internal diameter of the cannulated body. An opening of the groove facilitates to receive the cerclage cable therein. The width of the opening remains the same throughout an entire length of the continuous groove. The groove includes varying angle to facilitate unimpeded movement of cerclage cable therethrough.

9 Claims, 5 Drawing Sheets

(56) References Cited

U.S. PATENT DOCUMENTS

| | | | |
|---|---|---|---|
| 2004/0010264 A1 | 1/2004 | Acker et al. | |
| 2005/0171547 A1* | 8/2005 | Aram | A61B 17/8861 606/74 |
| 2005/0288674 A1* | 12/2005 | Golobek | A61B 17/8861 606/74 |
| 2006/0293691 A1* | 12/2006 | Mitra | A61B 17/8861 606/103 |
| 2007/0043377 A1* | 2/2007 | Fernandez | A61B 17/82 606/103 |
| 2007/0088362 A1* | 4/2007 | Bonutti | A61B 17/7053 606/99 |
| 2008/0208223 A1* | 8/2008 | Kraemer | A61B 17/82 24/712 |
| 2009/0306668 A1* | 12/2009 | Dell'Oca | A61B 17/8861 606/74 |
| 2017/0265918 A1* | 9/2017 | Dooney | A61B 17/04 |
| 2018/0153603 A1* | 6/2018 | Songer | A61B 17/8861 |
| 2018/0250053 A1* | 9/2018 | Schultz | A61B 17/06066 |
| 2019/0254728 A1* | 8/2019 | Skinner | A61B 17/56 |

\* cited by examiner

CABLE PASSER DEVICE

CROSS-REFERENCE TO RELATED APPLICATIONS

The present Application for Patent claims priority to U.S. Provisional Application No. 63/022,768 entitled "CABLE PASSER DEVICE" filed 11 May 2020, which is hereby expressly incorporated by reference herein.

BACKGROUND

1. Technical Field

The present disclosure relates generally to an orthopedic surgical instrument, and more particularly, to a cable passer device and method for placement of a cerclage cable for internal fixation of bone.

2. Description of the Related Art

Numerous tools and techniques are used in orthopedic surgery for internal fixation of bone fractures, including placement of plates, screws, pins, nails and wires. Depending upon the nature and location of the fracture, the fixation techniques or tools are selected. Cerclage wiring techniques are frequently used following reduction for provisional fixation of long bone fractures to stabilize the bone for placement of screws, nails or rods, after which the wires are removed.

Cerclage wires are passed around the bone to be secured with cannulated metal or plastic devices that are pushed through the tissues and around the bone. The cerclage wire passer device (also referred to as passer device) is pushed through the soft tissues until the tip of the device is available at anywhere from 90 to 270 degrees around the bone surface. In some embodiments of the passer device, a slot is formed at a handle of the device that communicates with the cannulated area of the device. The cable is passed through the slot and through the device to emerge from the opposite end of the passer device. Once the cable is located at the tip, it is retrieved and pulled around the rest of the bone. The passer device is then pulled in reverse around the bone again over the cable until the end of the cable fully emerges out from the passer.

The cable is then passed through a metal sleeve locking device, and tightly crimped to allow the tension to be maintained. In this scenario, the cable at both ends is manipulated with tightening and passing through a locking device. These maneuvers create the need for larger devices for locking, crimping and manipulation to secure the cable appropriately.

Few cerclage instruments and methods devised in recent years to facilitate the positioning and fixation of cerclage wire are discussed as follows. Beaded cables were designed to make the process simpler as the bead is preloaded onto the cable and abuts against the locking metal sleeve. Simple devices are required for tightening and securing the beaded cable. However, the beaded cable requires a broader exposure of the bone and soft tissues as the cable cannot be passed through the handle of most passers because the locking sleeve will not pass through the cannulated pathway.

An exemplary embodiment of a conventional cable passer device 200 is shown in FIG. 1. The device 200 comprises a cannulated body 202 including a straight portion 204 and an arcuate portion 206. A channel 208 extends radially from an internal diameter of the cannulated body 202. Referring to FIG. 2, the channel 208 includes an opening 210 to receive the cerclage cable 212. The width of the opening 210 and the angle of the channel 208 remains the same throughout the length of the channel 208.

Another view of the cable passer device 200 is shown in FIG. 3. Referring to FIG. 3, the cable 212 is fed into the channel 208. The device 200 enables the surgeon to pass the cable 212 around the bone. On locating the free end of the cable 212, the surgeon grasps both ends of the cable 212 and rotates the device 200 to a predefined degree to release the cable 212 from the channel 208. After the free end of the cable 212 is retrieved from the device 200, the device 200 is withdrawn by reversing the insertion motion. A disadvantageous aspect of the device 200 is that whenever the cable 212 is inserted within the channel 208, the cable 212 tends to collide with the inner surface of the channel 208 due to the uniform channel angle and channel width coupled with the tendency of the cable 212 to remain straight. As such, to facilitate the smooth passage of the cable 212 through the channel 208, the surgeon is required to move the device 200 in subtle clockwise and counter-clockwise directions while simultaneously moving the cable 212 within the channel 208 to allow the relative motion between the cable 208 and the channel 212 to maneuver the cable 212 out of the channel 208 from the distal end of the device 200. This is not desired as any movement of the device 200 inside the tissue surrounding the bone may result in inadvertent excessive dissection and damage to said tissue.

Accordingly, there is a need for a cable passer device and method for placement of a cerclage cable for internal fixation of bone that addresses the aforementioned shortcomings.

BRIEF SUMMARY

The present disclosure envisages a cable passer device for placement of a cerclage cable for internal fixation of bone. The cable passer device comprises a cannulated body including a proximal end and a distal end. The cannulated body further includes a straight portion extending from the proximal end, and an arcuate portion extending from the straight portion. A continuous groove extends from the proximal end to the distal end through the straight portion and the arcuate portion of the cannulated body. In one embodiment, the groove includes an opening to receive the cerclage cable, and a radius of the continuous groove remains the same throughout an entire length of the continuous groove. In one embodiment, the groove includes varying angles to facilitate unimpeded movement of cerclage cable therethrough.

The above summary contains simplifications, generalizations and omissions of detail and is not intended as a comprehensive description of the claimed subject matter but, rather, is intended to provide a brief overview of some of the functionality associated therewith. Other systems, methods, functionality, features and advantages of the claimed subject matter will be or will become apparent to one with skill in the art upon examination of the following figures and detailed written description.

BRIEF DESCRIPTION OF THE DRAWINGS

The description of the illustrative embodiments can be read in conjunction with the accompanying figures. It will be appreciated that for simplicity and clarity of illustration, elements illustrated in the figures have not necessarily been drawn to scale. For example, the dimensions of some of the elements are exaggerated relative to other elements. Embodiments incorporating teachings of the present disclosure are shown and described with respect to the figures presented herein, in which.

DETAILED DESCRIPTION

Figure 4:
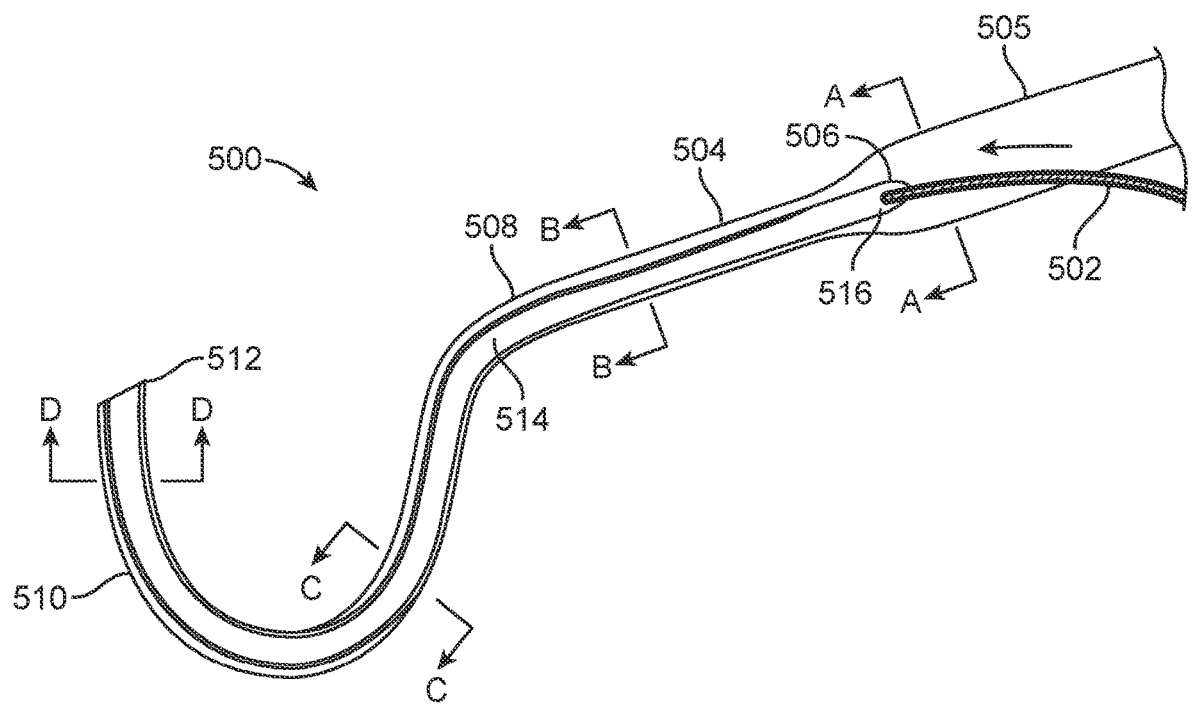
FIG. 4 shows a perspective view of a cable passer device, according to an embodiment of the present invention.

Referring to FIG. 4, the present invention discloses a cable passer device 500 and method for placement of a cerclage cable 502 for internal fixation of a bone. The device 500 comprises a cannulated body 504 including a proximal end 506, and a straight portion 508 extending from the proximal end 506. An arcuate portion 510 further extends from the straight portion 508, and the free end of the arcuate portion 510 is a distal end 512 of the device 500. In one exemplary embodiment of the present subject matter, the straight portion 508 and the arcuate portion 510 are machined from a single metal piece such that the straight portion 508 and the arcuate portion 510 together form an integral component.

The device 500 further comprises a handle 505 that is disposed at the proximal end 506 of the cannulated body 504 to facilitate manipulation of the device 500. The cannulated body includes a continuous groove 514 that extends from the proximal end 506 to the distal end 512. More specifically, the groove 514 extends along the length of the straight portion 508 as well as the arcuate portion 510 of the cannulated body 504. In one embodiment, the groove 514 extends from at least a portion of the handle 505 to the distal end 512 of the cannulated body 504.

In one embodiment, the groove 514 may have a circular cross-section that extends radially along an internal diameter of the cannulated body 504. In accordance with an embodiment of the present invention, the groove 514 has variable angle at one or more sections along the length of the straight portion 508 and the arcuate portion 510. As seen in FIG. 4, at different sections namely section A-A adjacent the proximal end 506, section B-B at a location on the straight portion 508, section C-C at a location on the arcuate portion 510, and section D-D the adjacent the distal end 512 are characterized with different angles. The different features and elaborate description of the aforementioned angles appear in the subsequent sections of the present disclosure.

The device 500 comprises an opening 516 for the groove 514 to facilitate reception of the cerclage cable 502 therein. In accordance with an embodiment of the present invention, the radius of the groove 514 remains the constant throughout an entire length of the continuous groove 514. As mentioned previously, the groove 514 includes varying angles provided at different sections. An advantageous aspect of these varying angles is that such variation facilitates an unimpeded movement of cerclage cable 502 through the groove 514. The groove 514 includes a lateral aperture that extends from the opening 516 to the distal end 512 and that is oriented to a left or right side In one or more embodiments, the lateral aperture has a width that is less than an internal diameter of the circular cross section of the groove 514.

Figure 5:
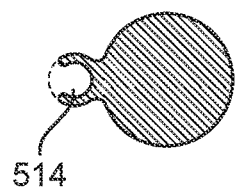
FIG. 5 shows a cross-sectional view of a groove along the line A-A of FIG. 4, according to an embodiment of the present invention.

FIG. 5 shows a cross-sectional view of the groove 514 along the line A-A of FIG. 4, according to an embodiment of the present invention. At section A-A, the angle of the groove 514, in accordance with the present disclosure, is a first angle and is considered as a reference angle in relation to which the angles at other sections are described.

Figure 6:
FIG. 6 shows a cross-sectional view of the groove along the line B-B of FIG. 4, according to an embodiment of the present invention.

FIG. 6 shows a cross-sectional view of the groove 514 at section B-B of FIG. 4, according to an embodiment of the present invention. The section B-B is taken at a location on the straight portion 508 of the cannulated body 504. The angle of the groove 514 at the section B-B is different from the angle of the groove 514 at section A-A. More specifically, the angle of the groove 514 at section B-B is rotated counter clockwise in relation to the first angle of the groove 514 at section A-A. In one embodiment, the angle of the groove 514 at section B-B is rotated counter clockwise in the range of 0 degree to 45 degrees.

It is to be noted that the version of the device 500 illustrated in FIG. 4 is configured for right handed usage. In a device 500 configured for left handed usage, the angle of the groove 514 at section B-B is rotated in a clockwise direction in relation to the angle of groove 514 at section A-A. Similarly to device 500, the angle of rotation ranges from 0 degrees to 45 degrees in a clockwise direction in relation to the angle of groove 514 at section A-A of the cable passer device configured for left handed usage in accordance with an embodiment of the present disclosure.

Figure 7:
FIG. 7 shows a cross-sectional view of the groove along the line C-C of FIG. 4, according to an embodiment of the present invention.

FIG. 7 shows a cross-sectional view of the groove 514 along the line C-C of FIG. 4, according to an embodiment of the present invention. The angle of the groove 514 at section C-C is substantially equal to the angle of the groove at section 514. It is to be noted that the angle of groove at section C-C remains the same for cable passer device 500 configured for left handed usage as well as right handed usage.

Figure 8:
FIG. 8 shows a cross-sectional view of the groove along the line D-D of FIG. 4, according to an embodiment of the present invention.

FIG. 8 shows a cross-sectional view of the groove 514 along the line D-D of FIG. 4, according to an embodiment of the present invention. The section D-D is taken at a location on the arcuate portion 510 of the cannulated body 504 adjacent the distal end 512. The angle of the groove 514 at the section D-D is different from the angle of the groove 514 at section A-A. More specifically, the angle of the groove 514 at section D-D is rotated clockwise in relation to the first angle of the groove 514 at section A-A. In one embodiment, the angle of the groove 514 at section D-D is rotated clockwise in the range of 0 degree to 45 degrees.

It is to be noted that the version of the device 500 illustrated in FIG. 4 is configured for right handed usage. In a device 500 configured for left handed usage, the angle of the groove 514 at section D-D is rotated in a counter clockwise direction in relation to the angle of groove 514 at section A-A. Similar to device 500, the angle of rotation ranges from 0 degrees to 45 degrees in a counter clockwise direction in relation to the angle of groove 514 at section A-A of the cable passer device configured for left handed usage in accordance with an embodiment of the present disclosure.

Figure 9:
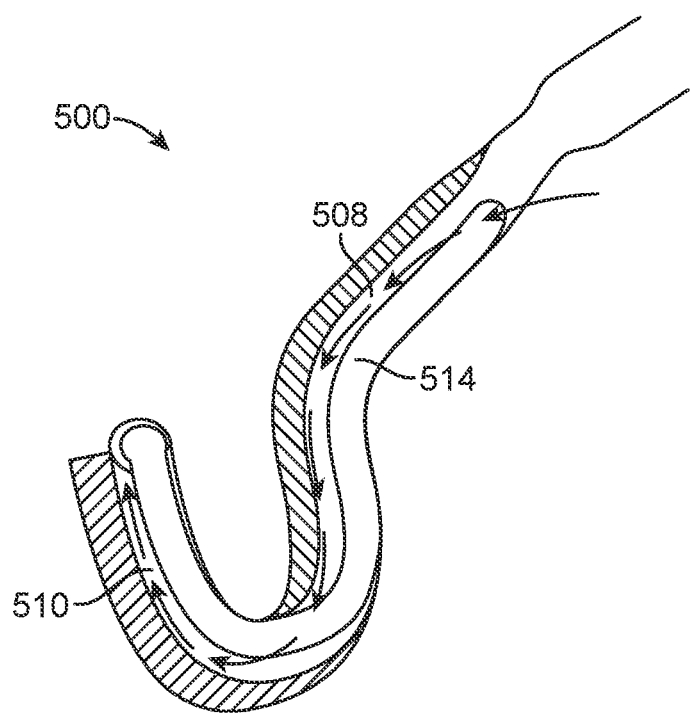
FIG. 9 shows a path of movement of cable at the groove of the cable passer device, according to an embodiment of the present invention.

FIG. 9 shows a path of movement of cable 502 at the groove 514 of the cable passer device 500, according to an embodiment of the present invention. The cerclage cable 502 is passed into the groove 514 through the opening 516. The cerclage cable 502 could be any type of cable including, but not limited to beaded cables 518, shown in FIG. 10. When either the beaded cable 518 or non-beaded cable 502 is passed across the device 500, the cable 502, which in its natural state tends to maintain a straight position, is pushed against the inner surface of groove 514, until the free end of the cable 502 is exposed out the other end of the groove 514. The varying groove angles at the proximal end 506, the straight portion 508, the arcuate portion 510, and the distal end 512 facilitate unimpeded movement of cerclage cable 502 in the groove 514 of the device 500. This movement of the cable 502 is indicated by the arrows in FIG. 9.

Figure 10:
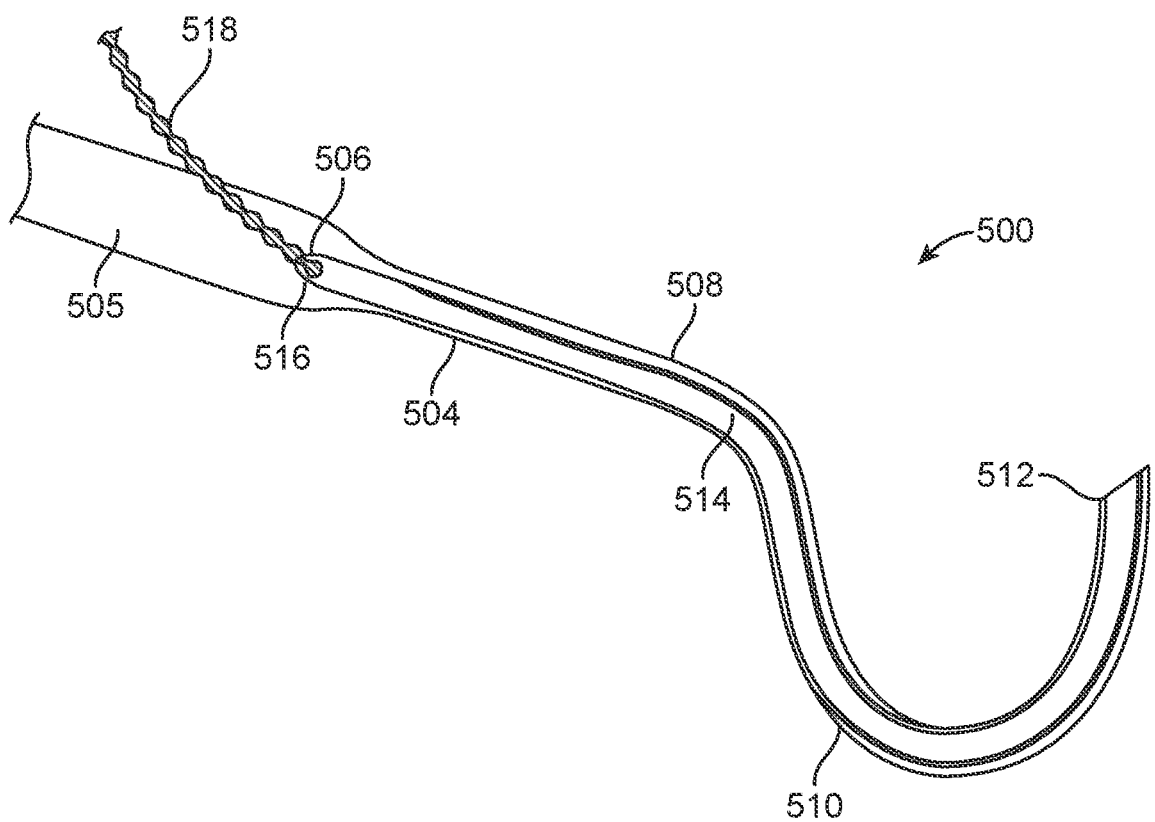
FIG. 10 shows the cable passer device receiving a beaded cable, according to another embodiment of the present invention.

FIG. 10 shows the cable passer device 500 receiving a beaded cable 518, according to another embodiment of the present invention. The device 500 facilitates passage of the beaded cable 518 through the groove 514 of the cannulated body 504 that can allow for the forward pass-through of the beaded cable 518 with minimal exposure, dissection, and damage to the muscle and soft tissues of the patient.

Figure 1:
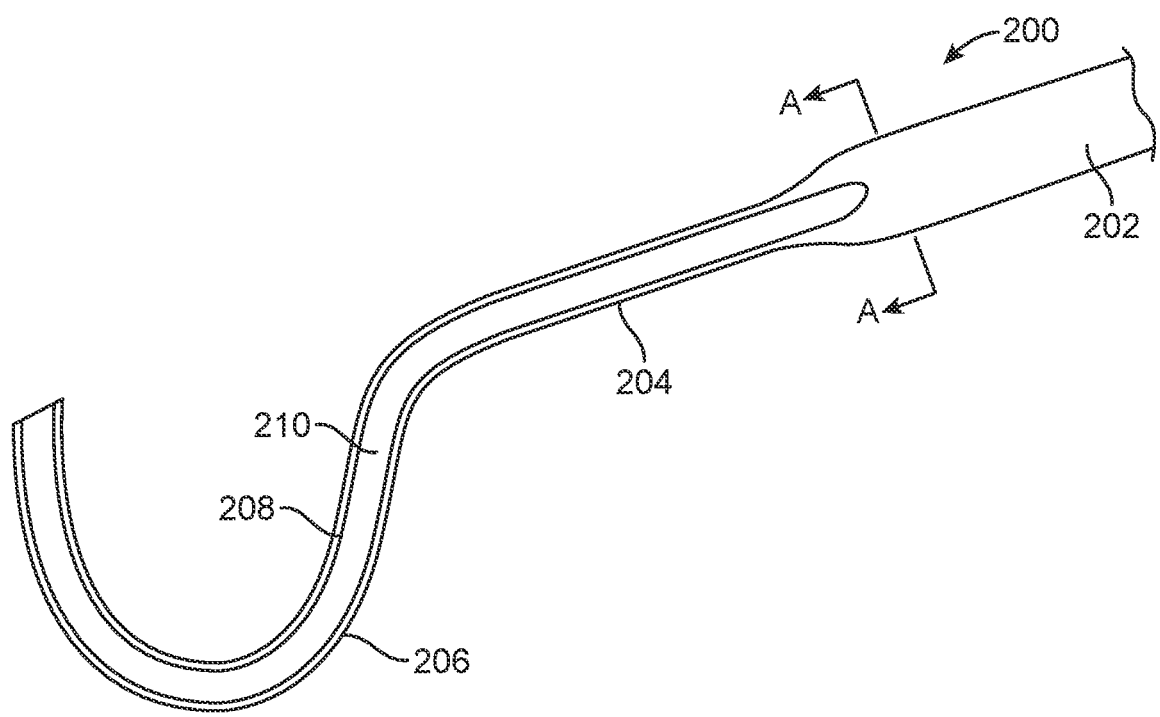
FIG. 1 shows a perspective view of a prior art cable passer device having an arcuate portion.
Figure 2:
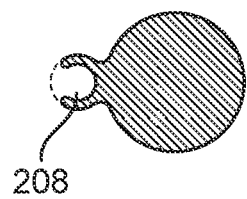
FIG. 2 shows a cross-sectional view of a channel along the line A-A of FIG. 1.
Figure 3:
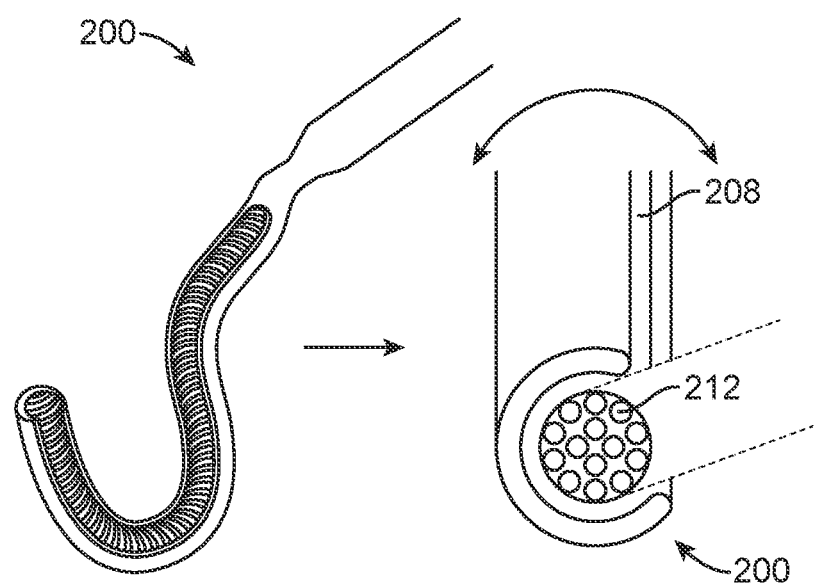
FIG. 3 shows the rotation of the prior art cable passer device to release the cerclage cable.
Figure 11:
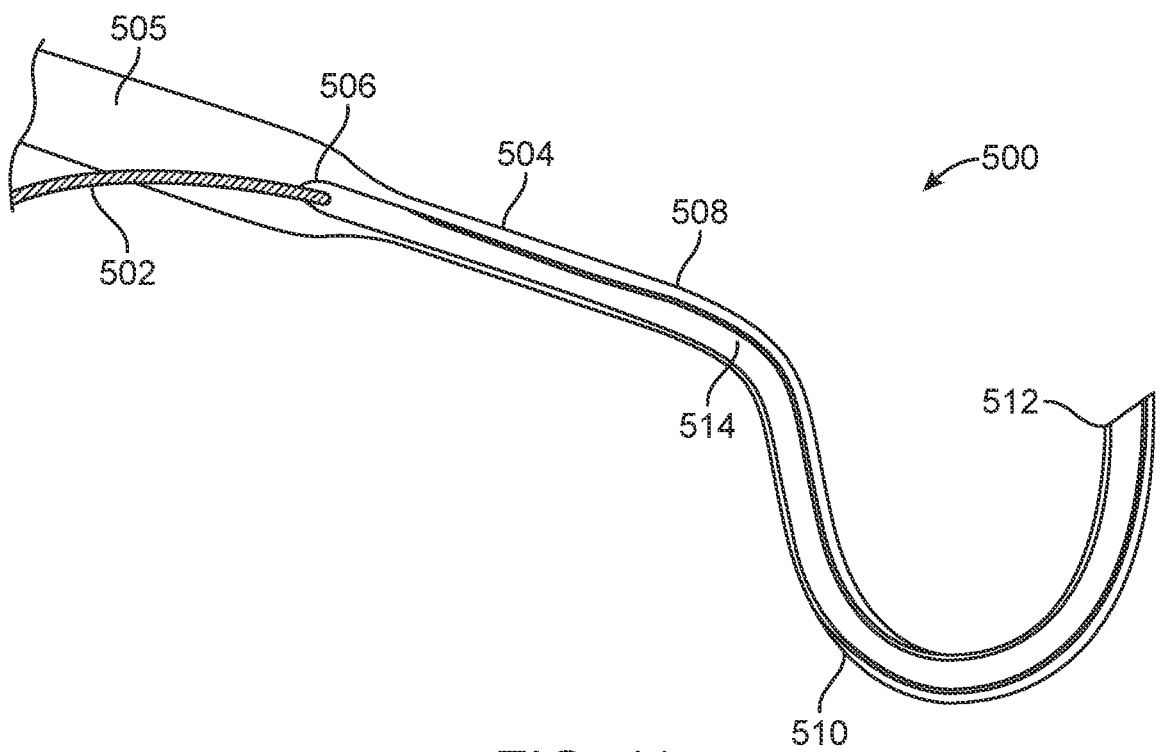
FIG. 11 shows the cable passer device operable by left-handed surgeons, according to another embodiment of the present invention.

The cable passer device 500 can be conveniently used by both right-handed and left-handed surgeons. FIG. 1 shows a perspective view of the cable passer device 500 operable by right-handed surgeons and FIG. 11 shows a perspective view of the cable passer device 500 operable by left-handed surgeons.

In one embodiment, the device 500 is preferably made of a biocompatible metal such as, for example, stainless steel or titanium. In one embodiment, cable (502, 518) is made from a blend of titanium or titanium alloy strands for a predetermined blend of flexibility and strength. In another embodiment, the cable (502, 518) could be made of any other material suitable for the surgery. In one embodiment, the cable (502, 518) is formed with a smooth surface to keep all cable (502, 518) strands tightly wound for eased entry into groove 514 of the device 500 and to prevent injury to the patient or surgeon.

The method of usage of the device 500 is hereinafter described. Initially, the surgeon prepares the area by exposing the patient's bone and performing any prerequisite tasks. The surgeon then grips the handle of the cable passer device 500 and inserts the arcuate portion 510 beneath the bone by hooking it around the bone and twisting his forearm until the point is exposed at the other side of the bone. The surgeon then takes the cable 502 and inserts the free end into a proximal end of the groove 514. The cable 502 could also be a beaded cable 518. As the cable 502 is fed into the groove 514, the passer device 500 guides the cable 502 around the bone until the free end is exposed out from the other end of the groove 514. The varying angle of the groove 514 enables the cable 502 to smoothly slide to the distal end 512 of the groove 514.

The resilience of the cable 502 along the bone and surrounding flesh and the variable angle of the groove 514 act in concert to prevent the cable 502 from disengaging from the groove 514 during this guided passing operation. Once the cable 502 is passed around the bone, the cable passer device 500 can be pulled back and the cable 502 will emerge from the groove 514. As such, the device 500 facilitates the unimpeded and guided passage of the cable 502 around the bone during surgeries to stabilize underlying fractures, bone defects, or places where stability of the bone is required.

The device 500 facilitates the use of metal, fibrous and plastic braided or smooth cables that are passed around bone during surgical needs to stabilize underlying fractures, bone defects or places where stability of the bone is required. The device 500 allows for the passage of the beaded cable 518 through the cannulated body 504 that can allow for the forward pass-through of the beaded cable 518 without exposure, dissection and damage to the skin, muscle and soft tissues. The cable passer device 500 could be effectively used in surgeries including, but not limited to, standard and minimally invasive orthopaedic surgeries. The cable passer device 500 could be used by both left-handed and right-handed surgeons.

In some embodiments, the distal end of the device is curved. In some embodiments, the curved distal end matches the curvature of a bone. In some embodiments, the curved distal end follows the shape of the bone. In some embodiments, the curved distal end forms a portion of a circumference of a circle (e.g., about 20%, 30%, 40%, 50%, 60%, 70%, 80%, or ranges incorporating any two of the aforementioned values, etc.). In some embodiments, the curved distal end encircles a portion of the bone. In some embodiments, the user's finger does not need to circumvent the entire bone. In some embodiments, the user circumvents only a portion of the bone (e.g., about 20%, 30%, 40%, 50%, 60%, 70%, 80%, or ranges incorporating any two of the aforementioned values, etc.). In some embodiments, the curved distal end is narrower than the appendage guide. In some embodiments, the curved distal end can provide minimally invasive separation of tissue adjacent to the bone. In some embodiments, the curved distal end can be closer to the bone during circumvention. In some embodiments, the curved distal end is inserted with a smaller incision.

In some embodiments, the curved distal end is blunt. In some embodiments, the curved distal end is pointed or sharpened. In some embodiments, the curved distal end can have a severe point. In some embodiments, the curved distal end has a low-profile configuration. In some embodiments, the curved distal end can separate tissue or muscle from the bone during movement. In some embodiments, the curved distal end can be inserted into a small space between bones and surrounding anatomical features. In some embodiments, the curved distal end has a flattened surface. In some embodiments, the flattened surface of the curved distal end can lie flat against the bone surface. In some embodiments, the curved distal end is shaped to pass the curved distal end through the linea aspera on the femur. In some embodiments, the curved distal end is shaped to pass the curved distal end through tissue or muscles. In some embodiments, the curved distal end is not able to penetrate bone. In some embodiments, the curved distal end is not able to penetrate an artery.

In some embodiments, the distal end of the device is curved to be passed around the bone. In some embodiments, the curved distal end is passed around the bone before the wire or cable is inserted into the cannulated body. In some embodiments, the curved distal end is passed around the bone after the wire or cable is inserted into the tube. In some embodiments, the curved distal end is passed around the bone and the wire is inserted in the other end of the device.

In some embodiments, the cannulated body and the curved distal end form a continuous channel. In some embodiments, the cannulated body and the curved distal end form a channel with a straight portion and a curved portion. In some embodiments, the cannulated body and the curved distal end form a smooth channel. An advantage is that the wire and/or cable can pass easily from the cannulated body to the curved distal end. In some embodiments, the device includes two cannulated bodies and two curved distal ends. In some embodiments, each cannulated body and corresponding curved distal end forms a continuous channel. In some embodiments, the device includes two separate channels. In some embodiments, the device includes two or more separate channels.

In some embodiments, the device allows two separate cables or wires to be passed. In some embodiments, the device allows two separate cables or wires to be passed simultaneously. In some embodiments, the device allows two separate cables or wires to be passed independently. In some embodiments, the device allows two different cables or wires to be passed (e.g., different dimensions, uses, etc.). In some embodiments, the device allows two similar or identical cables or wires to be passed. In some embodiments, each cable or wire is passed in a separate channel or lumen. In some embodiments, the device includes a dual lumen shaft. In some embodiments, the device includes two, separate cannulated bodies or channels. An advantage is that the wire or cable in separate cannulated bodies can reduce tangles of the wire or cable. In some embodiments, two or more cables or wires are passed in the same channel or lumen.

In some embodiments, the cannulated body and the curved distal end are formed of the same material. In some embodiments, the cannulated body and the curved distal end are formed of different materials. In some embodiments, the tube and the curved distal end are formed of the same material. In some embodiments, the tube and the curved distal end are formed of different materials. In some embodiments, the appendage guide and the cannulated body are formed of the same material. In some embodiments, the appendage guide and the cannulated body are formed of different materials. In some embodiments, the cannulated body and/or the curved distal end and/or the tube are formed of metal (e.g., titanium, stainless steel, etc.). In some embodiments, the cannulated body and/or the curved distal end and/or the tube are formed of plastic (e.g., PEEK, HDPE, etc.).

In some embodiments, the device is a wire passer. In some embodiments, the device is a cerclage wire passer. In some embodiments, the device is an orthopaedic wire passer. In some embodiments, the device is a 20, 25, 30, 35, 40, 45, 50, 55, or 60 mm wire passer. In some embodiments, the device is a large cable passer. In some embodiments, the device is a bone fixation wire passer. In some embodiments, the device is a universal wire passer.

Some conventional cables include an attached locking mechanism, such as on or near a proximal or distal end of a cable. The locking mechanism can permit adjustment and secondary re-tightening of the cable, which can be advantageous in some cases as the addition of more cable takes stress off the first cables, requiring them to be retightened. These locking devices are typically too large to fit through conventional cable passers. When the wire/cable is placed, the wire protruding from the device can be grasped to prevent it moving while the device is withdrawn. Various cables with locking mechanisms are commercially available and may be used. The wire/cable is then secured to the bone after tightening with the locking mechanism.

In some embodiments, the wire/cable passing device can preferably be made of a sterilizable material that could be disposed of, making the device "one use only." In other embodiments, the device can be made of, for example, a metal or other suitable material to allow for re-sterilization.

While the disclosure has been described with reference to exemplary embodiments, it will be understood by those skilled in the art that various changes may be made and equivalents may be substituted for elements thereof without departing from the scope of the disclosure. In addition, many modifications may be made to adapt a particular system, device or component thereof to the teachings of the disclosure without departing from the essential scope thereof. Therefore, it is intended that the disclosure not be limited to the particular embodiments disclosed for carrying out this disclosure, but that the disclosure will include all embodiments falling within the scope of the appended claims. Moreover, the use of the terms first, second, etc. do not denote any order or importance, but rather the terms first, second, etc. are used to distinguish one element from another.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The description of the present disclosure has been presented for purposes of illustration and description but is not intended to be exhaustive or limited to the disclosure in the form disclosed. Many modifications and variations will be apparent to those of ordinary skill in the art without departing from the scope of the disclosure. The described embodiments were chosen and described in order to best explain the principles of the disclosure and the practical application, and to enable others of ordinary skill in the art to understand the disclosure for various embodiments with various modifications as are suited to the particular use contemplated.

What is claimed is:

1. A cable passer device for placement of a cerclage cable for internal fixation of bone, comprising:
 a cannulated body including a proximal end,
 a straight portion extending from the proximal end,
 an arcuate portion extending from the straight portion, and a free end of the arcuate portion is a distal end of the device and
 a continuous groove extending along a length of the straight portion and the arcuate portion of the cannulated body,
  wherein the continuous groove comprises an opening on a side of the continuous groove to receive the cerclage cable, and the continuous groove comprises a lateral aperture from the opening to the distal end;
  wherein a radius of the continuous groove remains the same throughout an entire length of the continuous groove,
  wherein a groove angle of the continuous groove at a section A-A adjacent the proximal end of the cannulated body, at a section B-B at a location on the straight portion of the cannulated body, at a section C-C at a location on the arcuate portion of the cannulated body, and at a section D-D adjacent the distal end of the cannulated body are different from one another, to facilitate unimpeded movement of cerclage cable therethrough the groove, and wherein the groove angle at the section B-B of the cannulated body is rotated in a clockwise direction or a counterclockwise direction in relation to the groove angle at section A-A in the cable passer device, wherein the angle of rotation ranges from 0 degrees to 45 degrees, and wherein the groove angle is defined as an angle extending relative to a line perpendicular to a longitudinal axis of the device, which angle extends from a deepest point of the continuous groove through a center of the lateral aperture defined by the groove.

2. The cable passer device of claim 1, wherein the groove has a circular cross-section that extends radially along an internal diameter of the cannulated body.

3. The cable passer device of claim 1, wherein the proximal end of the cannulated body comprises a handle to facilitate manipulation of the device.

4. The cable passer device of claim 1, wherein the straight portion and the arcuate portion are machined from a single metal piece such that the straight portion and the arcuate portion together form an integral component.

5. The cable passer device of claim 1, wherein the cerclage cable is a beaded cable.

6. The cable passer device of claim 1, wherein the groove angle at the section C-C of the cannulated body is substantially equal to the groove angle at section A-A in the cable passer device.

7. The cable passer device of claim 1, wherein the groove angle at the section D-D of the cannulated body is rotated in a clockwise direction in relation to the groove angle at section A-A in the cable passer device, wherein the angle of rotation ranges from 0 degrees to 45 degrees.

8. The cable passer device of claim 1, wherein the groove angle at the section D-D of the cannulated body is rotated in a counterclockwise direction in relation to the groove angle at section A-A in the cable passer device, wherein the angle of rotation ranges from 0 degrees to 45 degrees.

9. The cable passer device of claim 2, wherein the lateral aperture has a width that is less than an internal diameter of the circular cross section of the continuous groove.

* * * * *